(12) United States Patent
Wieczorek

(10) Patent No.: US 6,659,115 B1
(45) Date of Patent: Dec. 9, 2003

(54) CLEANING AND STERILIZING MACHINE

(75) Inventor: Joachim Wieczorek, Willich-Anrath (DE)

(73) Assignee: SMEJA GmbH & Co. KG, Straelen-Herongen (DE)

( * ) Notice: Subject to any disclaimer, the term of this patent is extended or adjusted under 35 U.S.C. 154(b) by 0 days.

(21) Appl. No.: 09/958,684

(22) PCT Filed: Mar. 24, 2000

(86) PCT No.: PCT/EP00/02615

§ 371 (c)(1), (2), (4) Date: Dec. 12, 2001

(87) PCT Pub. No.: WO00/61199

PCT Pub. Date: Oct. 19, 2000

(30) Foreign Application Priority Data

Apr. 13, 1999 (DE) .......................... 199 16 720

(51) Int. Cl.⁷ ................................. B08B 3/04
(52) U.S. Cl. .................. 134/120; 134/133; 422/302
(58) Field of Search ................. 134/120, 133, 134/134, 201; 68/5 C, 171, 173, 210; 34/607, 608, 236; 422/270, 273, 302; 366/175.3, 180.1, 213, 200, 220

(56) References Cited

U.S. PATENT DOCUMENTS

| | | | |
|---|---|---|---|
| 3,992,148 A | * | 11/1976 | Shore et al. ............ 426/521 X |
| 4,642,828 A | * | 2/1987 | Lundberg |
| 5,130,093 A | * | 7/1992 | Wieczorek ............. 134/134 X |
| 5,516,207 A | * | 5/1996 | Habicht ..................... 366/213 |
| 6,030,578 A | * | 2/2000 | McDonald |

FOREIGN PATENT DOCUMENTS

| | | |
|---|---|---|
| CA | 2 083 541 A | 5/1993 |
| DE | 44 09 659 A | 9/1995 |
| DE | 198 24 724 A | 12/1999 |
| GB | 2 212 387 A | 7/1989 |

* cited by examiner

Primary Examiner—Frankie L. Stinson
(74) Attorney, Agent, or Firm—Proskauer Rose LLP

(57) ABSTRACT

This invention relates to a cleaning and sterilizing machine for small articles such as closure elements for pharmaceutical containers consisting of a treatment tank (1) which is supported by a horizontal shaft (3) in a carrier (2) and is mounted so it can rotate about the axis of the shaft (3) and has a funnel-shaped upper part (6) with a loading and unloading opening (8) arranged in it, said treatment tank being closeable by a valve (7) and having inlet and outlet lines (13, 14) for at least one treatment medium such as water, steam or compressed air connected to it and supported by the shaft (3). To prevent reloading of the cleaned small articles into a container so that the articles from the treatment tank (1) can be processed further, it is provided according to this invention that the shaft (3) has a supporting device (4) in which the treatment tank (1) is held detachably, and the inlet and outlet lines (13, 14) are detachably connected by couplings (10, 11) to valves (9, 10) arranged on the treatment tank (1). In this way the treatment tank itself can be transported to the machine for further processing, and the articles can be fed directly from it to this machine.

6 Claims, 3 Drawing Sheets

CLEANING AND STERILIZING MACHINE

Figure 1:
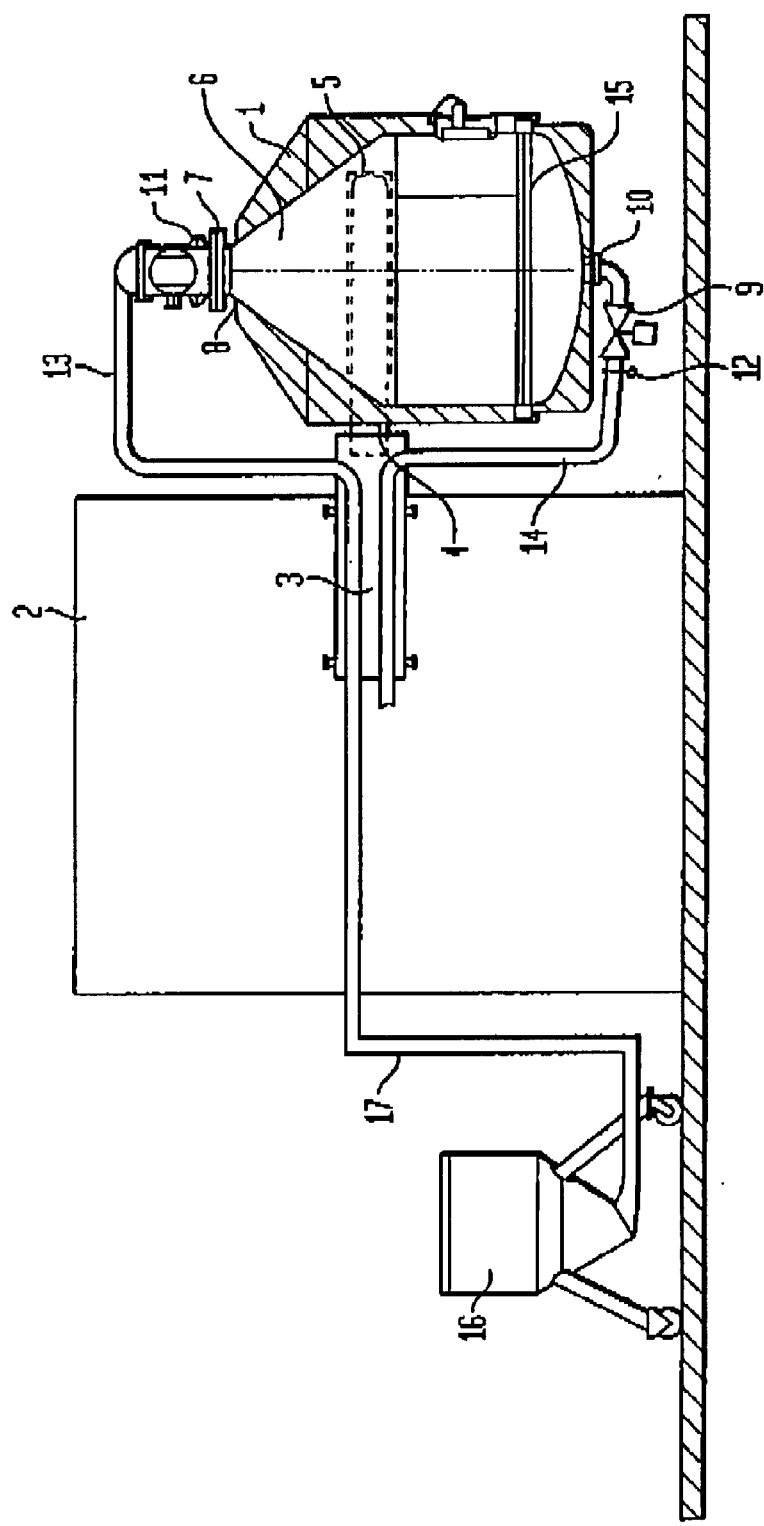

This invention relates to a cleaning and sterilizing machine for small articles such as the closure elements for pharmaceutical containers, said machine consisting of a treatment tank which is supported by a horizontal shaft in a carrier and is mounted so that it can pivot about the axis of the shaft, and which has a funnel-shaped top part with a loading and unloading opening which can be closed by a valve and is arranged in said top part and is connected to the inlet and outlet lines supported by the shaft for at least one treatment medium such as water, steam or compressed air.

In the production of pharmaceutical products, extremely high demands are made regarding the purity of the parts of the packaging such as the rubber stoppers. Simply washing the articles, e.g., in a rotary washing machine, and then drying the articles and sterilizing them, fails by far to meet these requirements. To more closely meet the requirements, special equipment has been developed for washing, sterilization and drying. Because of the risk of contamination, the loading and unloading devices, by means of which the articles to be cleaned are loaded into the machine and the cleaned articles are removed from the machine, are especially important.

European Patent 0 418,450 describes a cleaning and sterilizing machine of the abovementioned type in which the treatment tank is detachably, tightly and supportably connected through the loading and unloading openings to a container which holds the articles to be treated. After the treatment tank is pivoted 180 degrees, the articles to be treated fall out of the container and into the treatment tank beneath the container, where they are cleaned and sterilized together with the interior space of the connected container. By pivoting the treatment tank again, the cleaned articles are conveyed back into the container, which is uncoupled from the treatment tank after being hermetically sealed. Although this cleaning and sterilizing machine has the advantage that it need not be accommodated in a sterile compartment, it has the disadvantage of a great overall height, which is necessary to permit pivoting of the treatment tank connected to the container. Furthermore, another disadvantage is the need to transfer the sterile articles from the treatment tank to the container downstream from the cleaning and sterilization operation.

Furthermore, a cleaning and sterilizing machine with a comparatively low overall height is known from an unpublished state of the art document where the treatment tank is detachably but not rotatably mounted on a supporting device secured on a machine housing. In the upper area, the treatment tank has a loading opening that can be closed by a flap valve for the articles to be treated, and in the lower area it has an unloading opening that can be closed by a flap valve for the articles to be treated. Inlet and outlet lines for treatment media such as water, steam, etc. are provided in stationary mounts on the machine housing and are connected to the treatment tank by couplings. A basket designed as a screen that serves to hold the articles to be cleaned is arranged in the treatment tank. This basket has a funnel-shaped part so that it can be brought into correspondence with the loading or unloading opening by turning it in order to load or unload the articles to be treated into and out of the treatment tank. After the treatment is completed, the treatment tank, which has been hermetically sealed from the outside, is removed from the supporting device of the machine housing and can be transported at such to the site of use of the articles, e.g., to a pharmaceutical drug bottling installation. However, one disadvantage of the known cleaning and sterilizing machine is its complicated design with the rotating basket arranged in the interior of the treatment tank and with two separate loading and unloading openings.

The object of this invention is to create a cleaning and sterilizing machine that will require only a comparatively small overall height and is characterized by a simple and inexpensive design.

This object is achieved with a cleaning and sterilizing machine of the type defined in the preamble by the fact that the shaft has a supporting device in which the treatment tank is held detachably, and the inlet and outlet lines are connected detachably by couplings to valves arranged on the treatment tank.

Due to the fact that the treatment tank which is filled with articles to be cleaned can be hermetically sealed from the outside after the treatment and can be separated from the other components of the cleaning and sterilizing machine, this eliminates the complicated operations of loading and unloading the cleaning and sterilizing machine, which are associated with possible contamination of the articles to be cleaned as well as the machine itself. The great overall height of the known cleaning and sterilizing machines due to the loading and unloading operations is thus avoided. The treatment tank can be filled with the articles to be cleaned at any desired location in a non-sterile environment and can be conveyed directly to the site of use of the articles in a hermetically sealed and sterile state after cleaning. The treatment tank is characterized by a simple design. Because of the absence of moving parts, it is not subject to much wear. The loading opening also serves simultaneously as an unloading opening. The rotating basket in the interior of the treatment tank known in the state of the art is not necessary.

Figure 2:
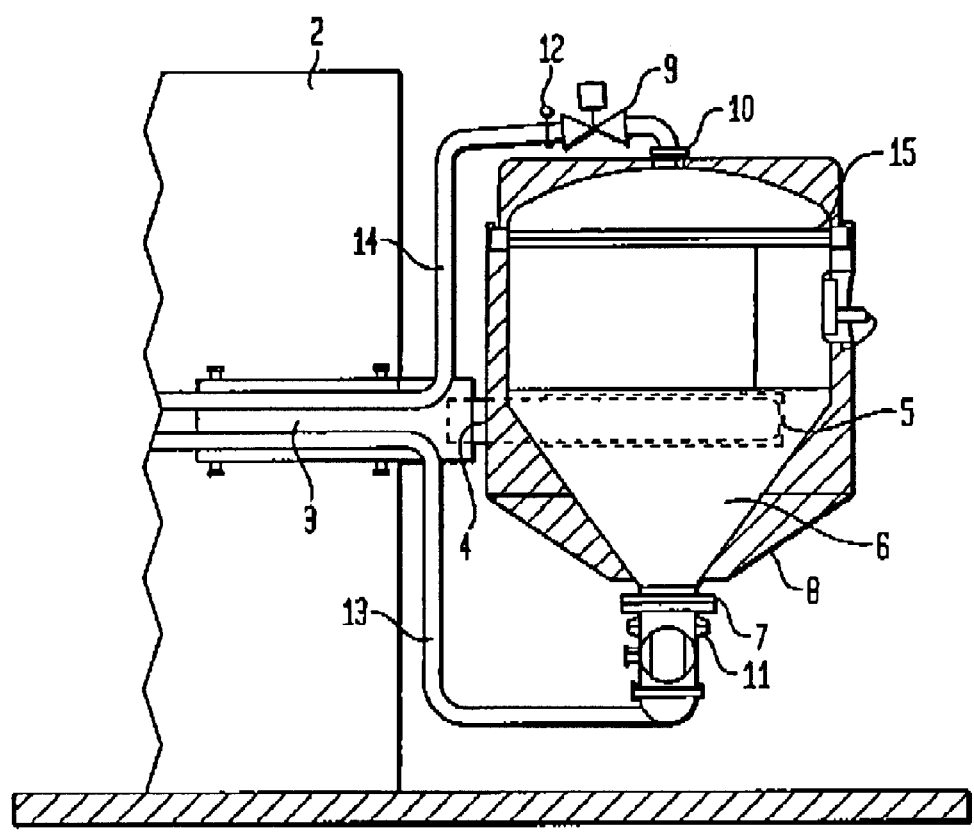
Figure 3:
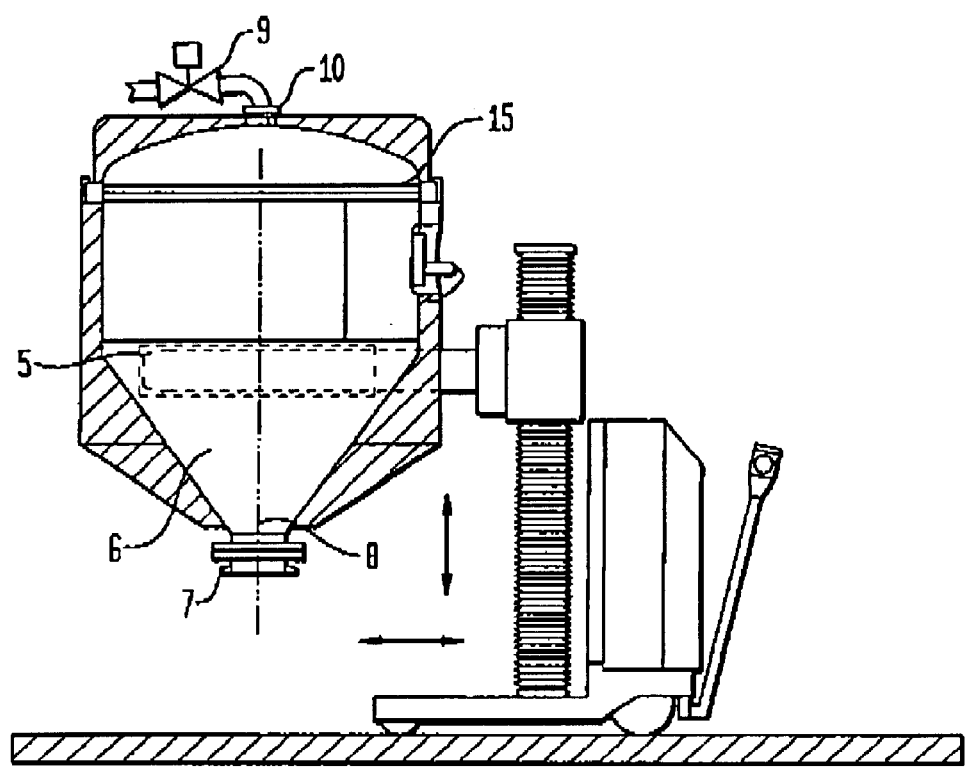

This invention is explained in greater detail below on the basis of schematic diagrams in the drawings, which illustrate one embodiment and show the following in particular:

FIG. 1: the cleaning and sterilizing machine, shown in a side view;

FIG. 2: a part of the machine illustrated in FIG. 1 in a side view with a treatment tank rotated by 180 degrees after the cleaning and sterilizing operation;

FIG. 3: a side view of the treatment tank from FIG. 2 which is mounted on a vehicle with a supporting frame but has been disconnected from the supporting device and the inlet and outlet lines of the cleaning and sterilizing machine.

The cleaning and sterilizing machine, which is set up in a non-sterilized environment, includes a treatment tank 1 and a horizontal shaft 3 which is mounted so that it can pivot in a machine housing 2 with the treatment tank 1 mounted on it. The horizontal shaft 3 has a fork 4. Tubular rails 5 are provided on the sides of treatment tank 1, so that the prongs of the fork 4, which is mounted on the shaft 3, can be inserted into these rails and locked there.

Treatment tank 1 has a funnel-shaped top part 6 with a loading and unloading opening 8 which can be closed by a pivotable flap valve 7. An opening 10 that can be closed by a valve 9 is provided on the bottom side of the treatment tank 1.

The loading and unloading opening 8 on the top side of the treatment tank 1 and the opening 10 on the bottom side of the treatment tank 1 are each provided on the side of a coupling 11, 12 facing away from the container. Inlet and outlet lines 13, 14 for water, steam and compressed air as treatment media coming from the media connections in the machine housing 2 can be connected tightly and in a self-supporting manner at the corresponding coupling parts of the treatment tank 1.

The articles to be treated are arranged on an extremely fine screen (pulsator) 15 which is positioned horizontally in a stationary mount between the two openings 8, 10 and extends over the entire cross section of the treatment tank 1, and this screen is placed in the treatment tank 1 which is in the treatment position according to FIG. 1.

The articles to be cleaned are loaded from a container 16 having a pneumatic system through inlet line 17 into the treatment tank 1.

The treatment is performed in a known way using water, steam or hot air plus optionally detergents and/or a silicone dispersion. Since the treatment, including the special guidance of the treatment media in the treatment tank 1 for the purpose of a thorough and gentle treatment of the articles is already known, it will be mentioned only briefly below.

FIG. 1 shows the cleaning and sterilizing machine immediately after insertion of the treatment tank 1 filled with the articles to be treated into the supporting device 4 of the horizontal shaft 3. The inlet and outlet lines 13, 14 are connected to the treatment tank 1 by means of the respective couplings 11, 12. The valves 7, 9, which remain closed until then, are opened for the treatment. Hot water and superheated steam are introduced in alternation through lines 13 and 14, thus cleaning the articles in a fluidized bed of steam.

After cleaning with hot water and superheated steam, the articles are siliconized with a dispersion in the fluidized bed at approximately 100° C. After the siliconization treatment is concluded, the silicone dispersion is forced downward with compressed air, which is supplied through line 13, and it is removed through the lower line 14.

After the siliconization treatment, ultrahigh purity steam is first supplied to the treatment tank 1 through the upper line 13 for sterilizing the articles, and then the steam is removed through the lower line 14 so that the flow of steam comes in contact with all the articles.

Then the articles are dried by introducing the sterile, filtered and heated compressed air into the treatment tank 1 through the upper line 13 and removing it by vacuum through the lower line 14 so that the stream of air comes in contact with all the articles.

To ensure that all the articles in the treatment tank 1 are uniformly treated by the treatment media, it is advantageous for the treatment tank 1 to be moved back and forth slowly during or between the individual treatment phases by rotating the horizontal shaft 3. This motion results in a thorough mixing of the articles.

After the treatment, the treatment tank is rotated 180 degrees, as illustrated in FIG. 2, while the valves 7, 9 are closed, the lines 13, 14 are uncoupled and the treatment tank 1 is removed from the fork 1 mounted on the shaft 3 with the help of a transport vehicle as illustrated in FIG. 3. The cleaned and sterilized articles are then hermetically sealed in the treatment tank 1, which is in turn in a non-sterilized environment. This tank can then be transported to the site of use of the articles, e.g., to a pharmaceutical drug bottling installation.

What is claimed is:

1. A cleaning and sterilizing machine for small articles, said machine comprising treatment tank which is supported by a horizontal shaft in a carrier and is mounted so that it can pivot about the axis of the shaft and which has a funnel-shaped upper part with a loading and unloading opening arranged in it such that it can be closed by a valve, and inlet and outlet lines for at least one treatment medium which are connected to the treatment tank and are supported by the shaft, wherein the shaft has a supporting device in which the treatment tank is held detachably and which permits pivoting about the axis of the shaft, and wherein the inlet and outlet lines are detachably connected by couplings to valves which are arranged on the treatment tank.

2. A cleaning and sterilizing machine according to claim 1, wherein the shaft has a fork as the supporting device in which the treatment tank is suspended.

3. A cleaning and sterilizing machine according to claim 1, wherein the treatment tank has lateral receptacles into which the prongs of the fork are inserted.

4. A cleaning and sterilizing machine according to claim 1, wherein the valve of the loading and unloading opening is arranged at the mouth of the funnel of the upper part.

5. A cleaning and sterilizing machine according to claim 1, wherein the small articles are closure elements for pharmaceutical containers.

6. A cleaning and sterilizing machine according to claim 1, wherein the treatment medium is water, steam, or compressed air.

\* \* \* \* \*